(12) United States Patent
Ouyang et al.

(10) Patent No.: US 12,102,628 B2
(45) Date of Patent: Oct. 1, 2024

(54) COMPOSITION AND METHODS FOR THE TREATMENT OF MYOPIA

(71) Applicant: Seinda Pharmaceutical Guangzhou Corporation, Guangdong (CN)

(72) Inventors: Hui Ouyang, Irvine, CA (US); Yong Qiu, San Diego, CA (US)

(73) Assignee: Seinda Pharmaceutical Guangzhou Corporation

( * ) Notice: Subject to any disclaimer, the term of this patent is extended or adjusted under 35 U.S.C. 154(b) by 0 days.

(21) Appl. No.: 17/706,225

(22) Filed: Mar. 28, 2022

(65) Prior Publication Data

US 2023/0062844 A1    Mar. 2, 2023

Related U.S. Application Data

(63) Continuation of application No. 16/632,105, filed as application No. PCT/US2018/043059 on Jul. 20, 2018, now Pat. No. 11,285,141.

(60) Provisional application No. 62/535,111, filed on Jul. 20, 2017.

(51) Int. Cl.
| | | |
|---|---|---|
| *A61P 27/02* | (2006.01) |
| *A61K 9/00* | (2006.01) |
| *A61K 31/06* | (2006.01) |
| *A61K 31/216* | (2006.01) |
| *A61K 31/222* | (2006.01) |
| *A61K 31/24* | (2006.01) |
| *A61K 31/4168* | (2006.01) |
| *A61K 31/417* | (2006.01) |
| *A61K 31/439* | (2006.01) |
| *A61K 31/4406* | (2006.01) |
| *A61K 31/46* | (2006.01) |
| *A61K 31/498* | (2006.01) |
| *A61K 31/551* | (2006.01) |
| *A61K 31/5513* | (2006.01) |
| *A61P 27/10* | (2006.01) |
| *C07C 217/20* | (2006.01) |
| *C07C 219/10* | (2006.01) |
| *C07D 213/04* | (2006.01) |
| *C07D 235/02* | (2006.01) |
| *C07D 403/04* | (2006.01) |
| *C07D 403/12* | (2006.01) |
| *C07D 471/08* | (2006.01) |
| *C07D 487/04* | (2006.01) |
| *C07D 491/18* | (2006.01) |

(52) U.S. Cl.
CPC ............ *A61K 31/46* (2013.01); *A61K 9/0048* (2013.01); *A61K 31/24* (2013.01); *A61K 31/4168* (2013.01); *A61K 31/417* (2013.01); *A61K 31/498* (2013.01); *A61K 31/551* (2013.01); *A61P 27/10* (2018.01)

(58) Field of Classification Search
CPC ........ A61P 27/02; A61P 27/10; A61K 9/0048; A61K 31/216; A61K 31/222; A61K 31/4168; A61K 31/417; A61K 31/439; A61K 31/4409; A61K 31/498; A61K 31/551; A61K 31/5513; A61K 45/06; A61K 2300/00; C07C 217/20; C07C 219/10; C07D 213/04; C07D 235/02; C07D 403/04; C07D 403/12; C07D 471/08; C07D 487/04; C07D 491/18
See application file for complete search history.

(56) References Cited

U.S. PATENT DOCUMENTS

| | | | |
|---|---|---|---|
| 6,273,092 B1 | 8/2001 | Nolan | |
| 8,299,079 B2 | 10/2012 | Kaufman | |
| 8,455,494 B2 | 6/2013 | Kaufman | |
| 9,089,562 B2 * | 7/2015 | Horn | A61K 31/165 |
| 9,320,709 B2 * | 4/2016 | Horn | A61K 31/498 |
| 9,833,441 B2 * | 12/2017 | Horn | A61K 31/439 |
| 10,610,518 B2 | 4/2020 | Robinson et al. | |
| 11,285,141 B2 | 3/2022 | Ouyang et al. | |
| 2006/0018839 A1 | 1/2006 | Ieni et al. | |
| 2007/0254914 A1 | 11/2007 | Wu | |
| 2009/0156606 A1 | 6/2009 | Sharma | |
| 2010/0298335 A1 | 11/2010 | Kaufman | |
| 2011/0053981 A1 | 3/2011 | Ieni | |
| 2011/0152274 A1 | 6/2011 | Kaufman | |
| 2014/0035225 A1 | 2/2014 | Kondo | |
| 2014/0036225 A1 | 2/2014 | Chehab | |
| 2015/0366854 A1 | 12/2015 | Ostrow | |
| 2016/0008278 A1 | 1/2016 | Horn | |
| 2016/0067238 A1 | 3/2016 | Wu | |
| 2019/0321337 A1 | 10/2019 | Robinson et al. | |

(Continued)

FOREIGN PATENT DOCUMENTS

| | | |
|---|---|---|
| CN | 105792815 | 7/2016 |
| EP | 1123705 | 8/2001 |

(Continued)

OTHER PUBLICATIONS

Asfar et al., "Determination of best regime for administration of atropine eye drops for cycloplegia," Adv. Ophthalmol. Vis. Syst., Jan. 2017, 6(1):42-45.

Benozzi et al., "Presbyopia: a new potential pharmacological treatment, "Medical Hypothesis, Discovery & Innovation Opthal. J., Jan. 2012, 1:1:3 pages.

Berge et al., "Pharmaceutical Salts", Journal of Pharmaceutical Science, 66: 1-19, 1977.

Broadley et al., "Muscarinic Receptor Agonists and Antagonists", vol. 6, No. 3, 148-185, 2001.

(Continued)

*Primary Examiner* — Brenda L Coleman
(74) *Attorney, Agent, or Firm* — Fish & Richardson P.C.

(57) ABSTRACT

Compositions and methods useful in slowing, inhibiting, or regressing the progression of myopia, while minimizing pupil dilation and light sensitivity are provided herein. Provided compositions can include a muscarinic receptor antagonist and a miotic agent.

15 Claims, No Drawings

(56) References Cited

U.S. PATENT DOCUMENTS

| | | | |
|---|---|---|---|
| 2020/0163951 A1 | 5/2020 | Ouyang |
| 2021/0030833 A1 | 2/2021 | Liu et al. |
| 2021/0308102 A1 | 10/2021 | Ouyang |

FOREIGN PATENT DOCUMENTS

| | | |
|---|---|---|
| JP | 02-025425 | 1/1990 |
| JP | 05-262751 | 10/1993 |
| JP | 2004530645 | 10/2004 |
| JP | 2010-514517 | 5/2010 |
| JP | 2013-144704 | 7/2013 |
| JP | 2016-529297 | 9/2016 |
| KR | 10 2001-0078803 | 8/2001 |
| KR | 10 2009-0019765 | 2/2009 |
| KR | 10 2009-0102810 | 9/2009 |
| KR | 10-2016-0045147 | 4/2016 |
| KR | 10-2017-0018962 | 2/2017 |
| WO | WO 2008/083118 | 7/2008 |
| WO | WO 2010/135731 | 11/2010 |
| WO | WO 2012/161655 | 11/2012 |
| WO | WO 2015/031186 | 3/2015 |

OTHER PUBLICATIONS

Cohen, "Management of errors of refraction with echothiophate iodide," Amer. J. of Ophthalmology, Aug. 1966, 62:2:303-312.

Drugs.com [online], "Cholinesterase Inhibitors," available on or before Jul. 16, 2017, via Internet Archive: Wayback Machine URL<http://web.archive.org/web/20170716205151/https://www.drugs.com/drug-class/cholinesterase-inhibitors.html.>, 7 pages.

Drugs.com [online], "Presbyopia", available on or before Jun. 30, 2016, via Internet Archive: Wayback Machine URL< http://web.archive.org/web/20160515000000*/https://www.drugs.com/health-guide/presbyopia.html>, retrieved on Jun. 28, 2022, 4 pages.

Extended European Search Report in Application No. 18836074.7, dated Jul. 7, 2020, 8 pages.

Extended European Search Report in European Appln. No. 19846256.6, dated Aug. 27, 2021, 9 pages.

International Preliminary Report and Written Opinion in International Application No. PCT/US2018/043059, dated Jan. 21, 2020, 7 pages.

International Preliminary Report on Patentability in Appln. No. PCT/US2019/045741, dated Feb. 9, 2021, 8 pages.

International Search Report and Written Opinion in Appln. No. PCT/US2019/045741, dated Oct. 15, 2019 , 9 pages.

International Search Report and Written Opinion in International Application No. PCT/US18/43059, dated Sep. 27, 2018, 12 pages.

International Search Report and Written Opinion in International Application No. PCT/US2019/045751, dated Oct. 15, 2019, 10 pages.

Liu et al., "a-Adrenergic Agonist Brinnonidine Control of Experimentally Induced Myopia in Guinea Pigs: A Pilot Study, Molecular Vision", 2017, 23:785-798.

[No Author Listed], "Acetylcholinesterase inhibitors," Meyler's Side Effects of Drugs, The International Encyclopedia of Adverse Drug Reactions and Interactions, Published 2016, 1 page.

Everydayhealth.com [online], "Can Presbyopia Be Prevented?" Apr. 19, 2022, retrieved on Apr. 3, 2023, retrieved from URL <https://www.everydayhealth.com/presbyopia/presbyopia-be-prevented/>, 12 pages.

Mayoclinic.org [online], "Presbyopia," Nov. 20, 2021, retrieved on May 23, 2023, retrieved from URL<https://www.mayoclinic.org/diseases-conditions/presbyopia/symptoms-causes/syc-20363328>, 4 pages.

* cited by examiner

COMPOSITION AND METHODS FOR THE TREATMENT OF MYOPIA

CLAIM OF PRIORITY

This application is a continuation of U.S. application Ser. No. 16/632,105 filed on Jan. 17, 2020, and is a 371 of international application PCT/US2018/043059, filed on Jul. 20, 2018, and claims the benefit of U.S. Provisional Patent Application Ser. No. 62/535,111, filed on Jul. 20, 2017. The entire contents of the foregoing are hereby incorporated by reference.

TECHNICAL FIELD

This disclosure relates to preventing, inhibiting, slowing, or regressing the progression of myopia in an eye.

BACKGROUND

Myopia describes the refractive error in which light entering the eye from distant objects is focused in front of the retina, leading to blurred vision. The condition is most commonly the result of excessive elongation of the posterior vitreous chamber of the eye, and increases the risk of retinal detachment and some degenerative retinal conditions. High myopia is a major cause of visual impairment and blindness. Myopia is also an important cause of reduced vision in populations throughout the world. In the United States, approximately 2% of the population is myopic at school entry and about 15% of the population entering high schools are myopic. Racial and ethnic differences in magnitude and prevalence of myopia have been observed. For example, the prevalence of myopia is greater in Asia than other parts of the world.

Juvenile-onset myopia typically develops at approximately six to eight years of age and progresses at a rate of approximately 0.50 D (diopters) per year through 15 to 16 years. The progression of myopia is typically faster at younger ages. Several factors have been suggested to have a role in the development of myopia. Many models estimate greater genetic effects than environmental effects for myopia. Children with two myopic parents have greater axial lengths, indicating a higher risk of myopia than children with one or no myopic parents. Environmental influences relate to prolonged reading or near work, which has been associated with increased myopia prevalence. Fewer hours spent outdoors also has been associated with myopia.

The management of myopia has been mostly directed at correcting the mismatch between the eye's optical power and its length using either optical means, such as single-vision spectacles and contact lenses, or refractive surgeries, such as photorefractive keratectomy (PRK) and laser-assisted in situ keratomileusis (LASIK), which both involve reshaping and thus modifying the optical power of the cornea. While these options restore sharp distance vision in myopes, they do nothing to control myopia progression. In terms of slowing myopia progression, multifocal spectacles and under-correction of myopic refractive error are thought to reduce accommodative error, which may act as a stimulus for increased eye growth.

While there are pharmaceutical agents that delay the progression of myopia by modulating the accommodation and regulating the axial length, there are currently no pharmaceutical agents FDA-approved in the U.S. for myopia treatment. Many of the pharmaceutical agents can cause side effects that make treatment impractical or unacceptable to patient populations.

SUMMARY

Provided herein are methods and compositions for modulating the accommodation of an eye and/or inhibiting and/or slowing axial lengthening of an eye of a subject, while minimizing side effects such as, e.g., pupil dilation and/or light sensitivity in the subject. In some aspects, the compositions and methods can be useful in treating, e.g., myopia in an effected eye. In some aspects, the compositions and methods can be useful preventing, inhibiting, slowing, or regressing the progression of myopia in an eye.

In one aspect, a composition is provided, the composition including a muscarinic receptor antagonist and a miotic agent.

In some aspects, the muscarinic receptor antagonist can be selected from the group consisting of a non-selective muscarinic receptor antagonist and a selective M3 muscarinic receptor antagonist. In some aspects, the muscarinic receptor antagonist can be a non-selective muscarinic receptor antagonist selected from the group consisting of atropine, cyclopentolate, homatropine, hyoscine, pirenzapine, anisodamine, tropicamide, pharmaceutically acceptable salts thereof, and combinations thereof. In some aspects, the muscarinic receptor antagonist can be a selective M3 muscarinic receptor antagonist selected from the group consisting of darifenacin, tiotropium, zamifenacin, J104129, DAU5884, pharmaceutically acceptable salts thereof, and combinations thereof.

In some aspects, the miotic agent can be selected from the group consisting of an alpha-1 adrenergic receptor antagonist, an alpha-2 adrenergic receptor agonist, a beta-adrenergic receptor antagonist, a nicotine receptor agonist, an antipsychotic, an anti-emetic, a cannabinoid, an MAO inhibitor, an EP1 receptor agonist, an EP4 receptor agonist, an FP receptor agonist, a calcium channel modulator, and combinations thereof. In some aspects, the miotic agent is selected from the group consisting of dapiprazole, thymoxamine, brimonidine, nicotine, apraclonidin, phentolamine, pharmaceutically acceptable salts thereof, and combinations thereof.

In some aspects, the muscarinic receptor antagonist is present in a concentration of from about 0.001% to about 2% (w/v). In some aspects, the miotic agent is present in a concentration of from about 0.001% to about 5% (w/v). In some aspects, the composition can further comprise a viscosity enhancer, a surfactant, or a combination thereof.

In some aspects the muscarinic receptor agonist can be atropine or a pharmaceutically acceptable salt thereof; and the miotic agent can be selected from the group consisting of brimonidine, bunazosin, thymoxamine, apraclonidine, phentolamine, combinations thereof, or pharmaceutically acceptable salts thereof.

In another aspect, a method is provided including administering to an eye of a subject, during a treatment period, a muscarinic receptor antagonist; and a miotic agent.

In some aspects the muscarinic receptor antagonist can be administered in an amount sufficient to inhibit, slow, or prevent progression of myopia in the eye, the muscarinic receptor antagonist is administered in an amount sufficient to inhibit or slow growth in the axial length of the eye, the miotic agent is administered in an amount sufficient to maintain pupillary dilation of less than about 7.5 mm in diameter, or a combinations thereof. In some aspects the muscarinic receptor antagonist and the miotic agent can be administered concurrently or sequentially.

In some aspects the treatment period can be from about 1 day to about 60 months. In some aspects the muscarinic receptor antagonist, the miotic agent, or a combination thereof can be administered from 1 to 6 times per day during the treatment period.

In some aspects, the method can further comprise treating the eye with an ocular device during at least a portion of the treatment period. In some aspects the ocular device can be a lens. In some aspects the method can further comprise correcting vision in the eye with a corrective lens during the treatment period.

In another aspect, a method of treating myopia is provided, including administering to an eye of a subject, during a treatment period, a muscarinic receptor antagonist; and a miotic agent.

The methods and compositions described herein provide several advantages. First, in some aspects, the methods and compositions described herein may inhibit or slow progression of myopia in an eye.

Second, in some aspects, the methods and compositions described herein may prevent myopia in at-risk subjects, such has subjects identified as having genetic factors for myopia development.

Third, in some aspects, the methods and compositions described herein may reduce, slow, or inhibit axial lengthening in an eye.

Fourth, in some aspects, the methods and compositions described herein may reduce pupillary dilation or other side effect symptoms in an eye receiving treatment or prophylactic treatment for myopia.

Fifth, in some aspects, the methods and compositions described herein may modulate the accommodation of an eye.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description, and from the claims.

DETAILED DESCRIPTION

The ciliary muscle receives only parasympathetic fibers from the short ciliary nerves that arise from the ciliary ganglion. Parasympathetic activation of muscarinic receptors causes ciliary muscle contraction, the effect of contraction is to decrease the diameter of the ring of ciliary muscle. In the human eye, the ciliary muscle controls the shape of the lens through suspended suspensory ligaments called zonules. The zonule fibers relax and the lens becomes more spherical, increasing its power to refract light for near vision. Like most smooth muscles, the ciliary muscle has a dual innervation, receiving both sympathetic and parasympathetic fibers. In ciliary muscle, the contraction necessary for accommodation is under parasympathetic or cholinergic control. Muscarinic receptors are presented in ciliary muscle, among which M3 is the predominant subtype and M1 is the minor subtype. Approximately two thirds of the muscarinic receptors in the human ciliary body are the M3 subtype. Lower levels (5% to 10%) of the M2 and M4 receptors are also present in these tissues. The M1 receptor (7%) has been detected in the ciliary muscle and pupillary muscle. The M5 receptor (5%) has been detected in the pupillary muscle. Therefore, muscarinic antagonists, such as atropine and pirenzepine, have been used to contract the ciliary muscle and treat myopia. Muscarinic antagonists have also been suggested to regulate the axial growth of a child's eye.

However, pharmaceutical agents can cause ocular side effects. In the human eye, there are the pupillary dilator muscle (a smooth muscle running radially in the iris that contracts, when stimulated, to widen the pupil, allowing for more light to pass through the eye) and the pupillary sphincter muscle (a smooth muscle running circular in the iris that contracts, when stimulated, to narrow the pupil, allowing for less light to pass through the eye). The pupillary dilator muscle is innervated by the sympathetic system, which acts by releasing noradrenaline that acts on α-receptors. The pupillary sphincter muscle is innervated primarily by the parasympathetic system. The M3, M1, and M5 receptors are the major subtypes of muscarinic receptors presented in the pupillary sphincter muscle. Therefore, some muscarinic antagonists used in myopia treatment also affect the function of the pupillary sphincter muscle and the pupillary dilator muscle, causing pupil dilation. Subjects with pupil dilation can experience the adverse side effects of glare and/or potential phototoxicity to the retina.

Muscarinic receptor antagonists (i.e., atropine and pirenzepine), dopamine agonists (i.e., apomorphine, bromocriptine, quinpirole and levodopa) and adenosine agonist (i.e., 7-methylxanthine) have been explored for use in myopic patients. In "Effects of different concentrations of atropine on controlling myopia in myopic children" (ShihY F, et al. Journal of Ocular Pharmacology and Therapeutics) 0.5% atropine solution has been reported to effectively slow the myopia progression. The results of Shih et al. are summarized in Table 1.

TABLE 1

Summary of Results of Shih et al.

| | Treatment group and control group Atropine concentration | | | |
|---|---|---|---|---|
| | 0.5% | 0.25% | 0.1% | Control (0%) |
| Myopia progression | 0.04 (diopter/yr) | 0.45 (diopter/yr) | 0.47 (diopter/yr) | 1.06 (diopter/yr) |

However, because of the pupil dilation drawbacks, patients generally experienced photophobia affecting their daily activities. Due to the side effects, the compliance of using atropine solution is poor and treatment dropout rate is high.

In recognition of the need for less severe cycloplegia and pupil dilation, the use of low concentration (e.g., 0.05% and 0.01%) atropine eye drops has also been explored (U.S. Pat. Appl. Publication No. 20070254914; U.S. Pat. Appl. Publication No. 20160067238; WO2012161655A1). Although less photophobia ratio was observed in the low concentration of atropine solution treatment, it was still significantly higher than the control group. Pupil dilation diameter was reported to be 5.52 mm in the treatment group using 0.05% atropine solution, significantly higher than the control group, which reported 2.93 mm pupil diameter. Photophobia ratio in the low concentration atropine group was still high, reported at about 66.67%, which could lead to poor compliance of the treatment.

In order to limit activity at the muscarinic receptors of the pupillary and ciliary muscles while more selectively blocking specific receptor subtypes for the treatment of myopia progression, this disclosure proposes a novel pharmaceutical composition to treat myopia while eliciting minimal adverse effects on the eye.

Provided herein are compositions including a muscarinic receptor antagonist and a miotic agent. Without wishing to be bound by theory, it is believed that the muscarinic receptor antagonist causes contraction of longitudinal fibers of the ciliary muscle by action on the muscarinic receptors. The compounds useful in practicing the present invention are any muscarinic antagonists. As used herein, the term "muscarinic antagonists" means any compound that produces a net sympatholytic response at autonomic neuro-effective junctions. Parasympatholytic agents, which block the parasympathetic system are muscarinic antagonists and parasympathomimetic agents which stimulate the parasympathetic system are muscarinic agonists. Neuro-effective junctions are considered cholinergic if energized by muscarinic agonists such as acetylcholine.

The iris has two sets of muscles: pupillary sphincter muscle that causes iris constriction and is supplied by the parasympathetic system such as muscarinic receptors, and pupillary dilator muscle that causes dilation of the iris and is supplied by the sympathetic system such as adrenergic receptors. Without wishing to be bound by theory, it is believed that in myopia treatment described herein, when a muscarinic receptor antagonist is used to modulate ciliary muscle to achieve normal accommodation and to regulate the axial length, the muscarinic receptor antagonist often relaxes the pupillary sphincter muscle to cause pupil dilation. Without wishing to be bound by theory, it is believed that, in some embodiments, a miotic agent that does not counteract the muscarinic activities should reduce the adverse effects of pupil dilation. For example, in some embodiments, an alpha receptor antagonist, as a miotic agent, may relax pupillary dilator muscle to reduce the pupil size. In some embodiments, the alpha receptor antagonist can working by a different mechanism and/or different signaling pathway, and thus it is believed the alpha receptor antagonist may not interfere with the effects of a muscarinic receptor antagonist on the pupillary sphincter muscle and/or reduction of axial lengthening. Therefore, without wishing to be bound by theory, it is believed that in some embodiments, the miotic agent can limit the pupillary dilation and light sensitivity that may be caused by the muscarinic receptor antagonist, without interfering with the muscarinic receptor antagonist's effect on slowing down the progression of myopia.

As used herein, "a", "an", "the", "at least one", and "one or more" are used interchangeably.

The terms "comprises" and variations thereof do not have a limiting meaning where these terms appear in the description and claims.

The terms "treat(ment)" or "treating" are used herein to denote delaying the onset of, preventing, inhibiting, alleviating the effects of, or regressing a disease or a symptom thereof in a subject.

The terms "therapeutically effective amount" and "effective amount" as used herein, refer to an amount or concentration of a composition or treatment described herein, utilized for a period of time (including acute or chronic administration and periodic or continuous administration) that is effective within the context of its administration for causing an intended effect or physiological outcome. For example, a therapeutically effective amount of a muscarinic receptor antagonist is an amount sufficient to inhibit, slow, or prevent progression of myopia in the eye. As another example, a therapeutically effective amount of a muscarinic receptor antagonist is an amount sufficient to inhibit or slow growth in the axial length of the eye. As another example, a therapeutically effective amount of a miotic agent is an amount sufficient to maintain pupillary dilation of, e.g., less than about 8 mm, less than about 7.9 mm, less than about 7.8 mm, less than about 7.7 mm, less than about 7.6 mm, less than about 7.5 mm, less than about 7.4 mm, less than about 7.3 mm, less than about 7.25 mm, less than about 7.2 mm, less than about 7.1 mm, less than about 7 mm, less than about 6.75 mm, or less than about 6.5 mm in diameter.

The term "subject" is used throughout the specification to describe an animal, human or non-human, to whom treatment according to the methods of the present disclosure is provided. Human and veterinary applications are anticipated by the present disclosure. The term includes but is not limited to birds, reptiles, amphibians, and mammals, e.g., humans, other primates, pigs, rodents, such as mice and rats, rabbits, guinea pigs, hamsters, horses, cows, cats, dogs, sheep, chickens and goats. In some embodiments, the subjects are humans, chickens, or mice. In some aspects, the subject is a human. Both pediatric and adult subjects are included. For example, in any of the methods described herein, the subject can be at least 6 months old (e.g., 6 months or older, 12 months or older, 18 months or older, 2 years or older, 4 years or older, 6 years or older, 10 years or older, 13 years or older, 16 years or older, 18 years or older, 21 years or older, 25 years or older, 30 years or older, 35 years or older, 40 years or older, 45 years or older, 50 years or older, 60 years or older, 65 years or older, 70 years or older, 75 years or older, 80 years or older, 85 years or older, 90 years or older, or 2, 3, 4, 5, 6, 7, 8, 9, 10, 12, 13, 14, 15, 16, 18, 20, 21, 24, 25, 27, 28, 30, 33, 35, 37, 39, 40, 42, 44, 45, 48, 50, 52, 55, 60, 65, 70, 75, 80, 85, 90, 95, 96, 97, 98, 99, 100, 101, 102, 103, or 104 years old).

In addition to individuals that have been diagnosed with myopia, individuals considered at risk for developing myopia may benefit from the present disclosure, e.g., because prophylactic treatment can begin before there is any evidence and/or diagnosis of the disorder. Individuals "at risk" include, e.g., individuals having genetic or environmental factors associated with development of myopia, such as individuals having at least one myopic parent, individuals spending limited time outdoors, individuals with longer axials lengths, and the like. Similarly, individuals in very early stages of myopia may benefit from prophylactic treatment.

Skilled practitioners will appreciate that a patient can be diagnosed, e.g., by a medical professional, e.g., a physician or nurse (or veterinarian, as appropriate for the patient being diagnosed), as suffering from or at risk for a condition described herein, e.g., myopia, using any method known in the art, e.g., by assessing a patient's medical history, performing diagnostic tests, and/or by employing imaging techniques. Various methods are known in the art to determine myopia and/or measure axial length.

Skilled practitioners will also appreciate that treatment need not be administered to a patient by the same individual who diagnosed the patient (or the same individual who prescribed the treatment for the patient). Treatment can be administered (and/or administration can be supervised), e.g., by the diagnosing and/or prescribing individual, and/or any other individual, including the patient her/himself (e.g., where the patient is capable of self-administration).

Also provided herein are pharmaceutical composition that include a muscarinic receptor antagonist and a miotic agent. A pharmaceutical composition is formulated to be compatible with its intended route of administration. Examples of routes of administration include ocular administration, e.g., topical ocular, injectable, ocular implant administration, or in combination with an ocular medical device such as a lens. As used herein the language "pharmaceutically acceptable carrier" includes solvents, dispersion media, isotonic and absorption delaying agents, and the like, compatible with pharmaceutical administration. Supplementary active compounds can also be incorporated into the compositions.

The compositions and methods described herein include muscarinic receptor antagonists. Muscarinic receptor antagonists are parasympatholytic and block the parasympathetic system. These antagonists have a higher affinity for the muscarinic receptors, but they also bind to the other receptor subtypes with a lower affinity. Combinations of muscarinic receptor agonists may also be used in some aspects of the composition and methods described herein. Pharmaceutically acceptable salts of muscarinic receptor agonists may also be used in some aspects of the composition and methods described herein. Non-limiting examples of muscarinic receptor antagonists useful in some aspects of the compositions and methods disclosed herein include 4-DAMP, abediterol, aclidinium bromide, AFDX-384, amitriptyline, amoxapine, arketamine, atropine, benzatropine, benzilylcholine mustard, bevonium, bornaprine, brompheniramine, cyanodothiepin, cyclopentolate, darifenacin, desfesoterodine, dexetimide, dicycloverine, dimenhydrinate, diphemanil metilsulfate, diphenhydramine, emepronium bromide, etybenzatropine, fesoterodine, flavoxate, glycopyrronium bromide, hexocyclium, himbacine, homatropine, hyoscine, hyoscyamine, imidafenacin, imipramine, indacaterol/glycopyrronium bromide, ipratropium bromide, medrylamine, mepenzolate, methantheline, methoctramine, methylatropine, methylhomatropine, octatropine methylbromide, olanzapine, orphenadrine, otilonium bromide, oxybutynin, oxyphenonium bromide, PD-102807, PD-0298029, penthienate, pipenzolate bromide, piperidolate, pirenzepine, poldine, prifinium bromide, procyclidine, propantheline bromide, propiomazine, solifenacin, telenzepine, tiemonium iodide, tiotropium bromide, tolterodine, trihexyphenidyl, triptiramine, tropicamide, umeclidinium bromide, vedaclidine, zamifenacin, and the like, and/or a pharmaceutically acceptable salt of any one of the preceding compounds.

In some aspects, the muscarinic antagonists include, but are not limited to, atropine, cyclopentolate, homatropine, hyoscine, pirenzapine, anisodamine, tropicamide, and/or a pharmaceutically acceptable salt of any one of the preceding compounds.

A summary of the properties of some muscarinic receptor antagonists appears in Table 2:

TABLE 2

| Compound | MW | Concentration (w/v) | Exemplary Dosing Frequency | Acting Duration |
|---|---|---|---|---|
| Scopolamine | 303.4 | 0.25% | Daily | longer than atropine |
| Atropine | 289.4 | 0.1%, 0.5%, 1% | Daily | 7-14 days |
| Cyclopentolate | 291.4 | 0.5%, 1% | Daily | 4 days |
| Homatropine | 356.3 | 2% | Daily | — |
| Tropicamide | 284.4 | 0.5% | Daily | 1 day |
| Pirenzepine | 351.4 | 2% (gel) | Twice a day | <1 day |

In some aspects, the muscarinic receptor antagonist can include an M3 receptor selective antagonist, a combination of M3 receptor selective antagonists, or combinations of M3 receptor selective antagonist(s) with one or more other muscarinic receptor antagonist(s), such as a non-selective muscarinic receptor antagonist. Non-limiting examples of M3 receptor selective antagonists include darifenacin, tiotropium, zamifenacin, J104129 ((2R)—N-[1-(4-methyl-3-pentenyl)piperidin-4-yl]-2-cyclopentyl-2-hydroxy-2-phenylacetamide), DAU5884 (8-Methyl-8-azabicyclo-3-endo [3.2.1]oct-3-yl-1,4-dihydro-2-oxo-3(2H)-quinazolinecarboxylic acid ester), and the like, and/or a pharmaceutically acceptable salt of any one of the preceding compounds.

A summary of the properties of some M3 receptor-selective antagonists appears in Table 3:

TABLE 3

| Compound | Structure | MW | logP | Aqueous Solubility | Affinity (pKi) |
|---|---|---|---|---|---|
| Darifenacin | 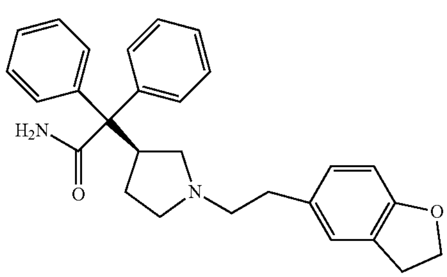 [SMILES: NC(=O)C(c1ccccc1)(c1ccccc1)[C@@H]1CCN(CCc2ccc3c(c2)CCO3)C1] | 426.6 | 4.5 | 6.03 mg/mL | 9.4 |

TABLE 3-continued

| Compound | Structure | MW | logP | Aqueous Solubility | Affinity (pKi) |
|---|---|---|---|---|---|
| Zamifenacin | (structure) | 415.5 | 4.4 | 0.02 mg/mL | 9.3 |
| Tiotropium | (structure) | 472.4 | −1.8 | 25 mg/mL | 8.2 |

Analogs of the muscarinic receptor antagonists that function as muscarinic antagonists are also embraced by the compositions and methods described herein. The ability of such analogs to slow down the progression of myopia can be tested easily using methods known in the art.

The compositions and methods described herein include miotic agents. A miotic agent is a compound or composition that can contract the pupillary dilator muscle. In some aspects, the miotic agent is a miotic agent that does not counteract the muscarinic activities of the muscarinic receptor antagonist. In some aspects, the miotic agent is not a muscarinic agonist. In some aspects, the miotic agent does not interfere with the activities of muscarinic antagonist. In some aspects, the miotic agent is not a cholinesterase inhibitor, which might interfere with the activities of muscarinic antagonist. Exemplary miotic agents useful in the methods and compositions described herein include, but are not limited to, alpha-1 receptor antagonists, alpha-2 receptor antagonists, β-adrenergic receptor antagonists, nicotine receptor agonists, adenosine receptor antagonists, antipsychotics, anti-emetics, cannabinoids, monoamine oxidase (MAO) inhibitors, EP1 receptor agonists, EP4 receptor agonists, and FP receptor agonists, and/or a pharmaceutically acceptable salt of any one of the preceding compounds.

Non-limiting examples of alpha-1 receptor antagonist include phenoxybenzamine, phentolamine, tolazoline, trazodone, alfuzosin, dapiprazole, thymoxamine, doxazosin, prazosin, tamsulosin, bunezosin, terazosin, trimazosin, silodosin, atipamezole, idazoxan, mirtazapine, yohimbine, carvedilol, labetalol, urapidil, abanoquil, adimolol, ajmalicine, amosulalol, arotinolol, atiprosin, benoxathian, buflomedil, bunazosin, carvedilol, CI-926, corynanthine, DL-017, domesticine, eugenodilol, fenspiride, GYKI-12743, GYKI-16084, indoramin, ketanserin, L-765314, mephendioxan, metazosin, monatepil, naftopidil, nantenine, neldazosin, nicergoline, niguldipine, pelanserin, phendioxan, piperoxan, quinazosin, ritanserin, RS-97078, SGB-1534, SL-890591, spiperone, talipexole, tibalosin, tiodazosin, tipentosin, tolazoline, upidosin, zolertine, and the like, and/or a pharmaceutically acceptable salt of any one of the preceding compounds.

Non-limiting examples of alpha-2 receptor agonists include apraclonidine, brimonidine, clonidine, mivazerol, naphazoline, oxymetazoline, tetrahydrozoline, guanfacine, guanabenz, guanoxabenz, guanethidine, xylazine, tizanidine, medetomidine, methyldopa, methylnorepinephrine, moxonidine, rilmenidine, fadolmidine, dexmedetomidine, amitraz, cannabivarin, detomidine, dihydroergotamine, dipivefrine, dopamine, ephedrine, ergotamine, esproquin, etilefrine, eEthylnorepinephrine, 6-fluoronorepinephrine, levonordefrin, lofexidine, naphazoline, 4-NEMD, (R)-3-nitrobiphenyline, norepinephrine, phenylpropanolamine, piperoxan, pseudoephedrine, rilmenidine, romifidine, talipexole, tetrahydrozoline, tolonidine, xylometazoline, and the like, and/or a pharmaceutically acceptable salt of any one of the preceding compounds.

Non-limiting examples of β-adrenergic receptor antagonists include acebutolol, atenolol, betaxolol, bisoprolol, carteolol esmolol, isoproterenol, levobunolol, metoprolol, penbutolol nadolol, nebivolol, pindolol, propranolol, timolol, sotalol, and the like, and/or a pharmaceutically acceptable salt of any one of the preceding compounds.

Non-limiting examples of nicotine receptor agonist include nicotine, varenicline, galantamine, epibatidine, lobeline, decamethonium, cytosine, nifene, dimethylphenylpiperazinium, and the like, and/or a pharmaceutically acceptable salt of any one of the preceding compounds.

Non-limiting examples of adenosine receptor antagonists include 7-methylxathine, caffeine, theophylline, theobromine, and the like, and/or a pharmaceutically acceptable salt of any one of the preceding compounds.

Non-limiting examples of antipsychotics include risperdal, haloperidol, thorazine, olanzapine, quetiapine, mirtazapine, chlorpromazine, prochlorperazine, alizapride, metoclopramide, midazolam, lorazepam, and the like, and/or a pharmaceutically acceptable salt of any one of the preceding compounds.

Non-limiting examples of anti-emetics include ondansetron, droperidol, metoclopramide, dolasetron, granisetron, tropisetron, palonosetron, domperidone, aprepitant, casopitant, rolapitant, cyclizene, diphenhydramine, dimenhydinate, doxylamine, meclizine, promethazine, hydroxylzine, and the like, and/or a pharmaceutically acceptable salt of any one of the preceding compounds.

Non-limiting examples of cannabinoids include cannabis, dronebinol, nabilone, sativex, and the like, and/or a pharmaceutically acceptable salt of any one of the preceding compounds.

Non-limiting examples of monoamine oxidase (MAO) inhibitors include selegiline, befloxatone moclobemide, isocarboxazid, nialamide, pheneizine, hydracarbazine, traylcypromine, bifemelane, pirlindole, toloxatone, rasagiline, linezolid, methylene blue, and the like, and/or a pharmaceutically acceptable salt of any one of the preceding compounds.

Non-limiting examples of EP1 receptor agonists, EP4 receptor agonists, and FP receptor agonists include PGE2, PGE1, PGF2α, PGD2, PGE2, PGI2, TXA2, cloprostenol, flupostenol, latanoprost, tafluprost, enprostil, sulprostone, U46619, carbacyclin, and iloprost, ONO-D1-OO4, 1-hydroxy-$PGE_1$, rivenprost (ONO-4819), OOG-308, ONO-AE1-329, AGN205203, ONO-4819, CP-734432, AE1-329, SC-19220, SC-51089, EP4RAG, and the like, and/or a pharmaceutically acceptable salt of any one of the preceding compounds.

Non-limiting examples of others miotic agents useful in the compositions and methods described herein include camptothecin and derivatives (cancer drug), ionomysin (Ca2+ channel modulator), thapsigargin (Ca2+ channel modulator), reserpine (norepinephrine depleting agents), and the like, and/or a pharmaceutically acceptable salt of any one of the preceding compounds.

Analogs of the miotic agents that function as miotic agents are also embraced by the compositions and methods described herein. The ability of such analogs to prevent, or inhibit excessive pupil dilation when used in combination with a muscarinic receptor antagonist in the compositions and methods described herein can be tested easily using methods known in the art.

The muscarinic agonists or miotic agents described herein may be administered per se or in the form of a pharmaceutically acceptable salt. When used in a formulation, the salts should be both pharmacologically and pharmaceutically acceptable, but non-pharmaceutically acceptable salts may be conveniently used to prepare the active free compound or pharmaceutically acceptable salts thereof. A "pharmaceutically acceptable salt" is any salt that retains the activity of the parent compound and does not impart any additional deleterious or untoward effects on the subject to which it is administered and in the context in which it is administered compared to the parent compound. Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. The term "pharmaceutically acceptable salt" is also meant to include salts of active compounds which are prepared with relatively nontoxic acids or bases, depending on the particular substituent moieties found on the compounds described herein. When compounds useful in the compositions and methods described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds useful in the compositions and methods described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66:1-19) which is incorporated by reference. In some aspects, compounds useful in the compositions and methods described herein may contain both basic and acidic functionalities that allow the compounds to be converted into either base or acid addition salts.

Many of the compounds of the described herein are known in the art for their purposes, and are known to be safe under ordinary conditions of use. Thus, in some aspects, the treatment of this invention can be administered by substantially conventional means, consistent with known eye treatments, while avoiding irritation, discomfort of the need for unusual application procedures.

The compositions described herein containing muscarinic receptor antagonists and/or a miotic agent and can, in some aspects, be formulated as ophthalmological compositions or formulations. In some aspects of the methods described herein, the muscarinic receptor antagonists and miotic agents can be provided in separate formulations. Formulations useful for the compositions and methods described herein may include any formulation, in which the compositions and/or compounds described herein may be delivered to the eye. In some aspects, the muscarinic agonists and/or miotic agents of the present invention are applied to the eye in a topical preparation. By a topical preparation, it is meant a preparation, which is adapted to be applied to the surface of the eye.

In some aspects of topical preparations described herein, therapeutic compounds of the preparation can contact the surface of the eye and penetrate into the deeper tissues of the eye. In some aspects, topical preparations have liquid carriers and can be aqueous solutions or suspensions, or emulsions. In some aspects, topical preparations can include a solution, a suspension, an emulsion, a gel, or a sustained release formulation, including, e.g., an implants or an ocular device such as a lens. In some aspects, the muscarinic agents and/or miotic agents described herein can be provided in formulations that enhance the duration of activity of the composition on neuro-effective junctions. Accordingly, such formulations may include any of the muscarinic antagonists or miotic agents described herein.

The compounds of the present invention may be applied in a pharmaceutically acceptable ophthalmic preparation. A pharmaceutically acceptable ophthalmic preparation can, in some aspects, produce medically desirable therapeutic effects without concurrently causing clinically significant adverse effects. Clinically significant adverse effects refer to unacceptable side effects of the preparation, including either medically or cosmetically unacceptable effects. Examples of unacceptable side effects include reddening or irritated eyes, impaired long distance vision, elevated intraocular pressure, brow ache, excessive pupillary dilation, unacceptable light sensitivity, and the like. In some embodiments, exemplary pupillary dilation of greater than 7.5 mm in diameter is considered to be excessive.

The compounds of the present invention can be administered in therapeutically effective amounts. As described above therapeutic effective amount includes, in some aspects, an amount that slows down the progression of myopia with minimal pupil dilation. Compounds are typically added to the ophthalmic preparations of the invention in concentrations of between about 0.001% and about 5% by weight of the entire formulation.

In some aspects, the muscarinic receptor antagonist is present in a composition or formulation described herein at a concentration of from about 0.001% to about 5%, from about 0.001% to about 4%, from about 0.001% to about 3%, from about 0.001% to about 2%, from about 0.001% to about 1.5%, from about 0.001% to about 1%, from about 0.001% to about 0.5%, from about 0.001% to about 0.2%, from about 0.001% to about 0.1%, from about 0.001% to about 0.05%, from about 0.001% to about 0.01%, from about 0.001% to about 0.005%, from about 0.01% to about 0.05%, from about 0.01% to about 0.1%, from about 0.05% to about 0.1%, from about 0.1% to about 1%, about 0.001%, about 0.002%, about 0.005%, about 0.01%, about 0.05%, about 0.1%, about 0.5%, about 1%, about 1.1%, about 1.5%, about 1.8%, about 2%, about 3%, about 4%, or about 5%, by weight of the composition or formulation.

In some aspects, the miotic agent is present in a composition or formulation described herein at a concentration of from about 0.001% to about 5%, from about 0.001% to about 4%, from about 0.001% to about 3%, from about 0.001% to about 2%, from about 0.001% to about 1.5%, from about 0.001% to about 1%, from about 0.001% to about 0.5%, from about 0.001% to about 0.2%, from about 0.001% to about 0.1%, from about 0.001% to about 0.05%, from about 0.001% to about 0.01%, from about 0.001% to about 0.005%, from about 0.01% to about 0.05%, from about 0.01% to about 0.1%, from about 0.05% to about 0.1%, from about 0.1% to about 1%, about 0.001%, about 0.002%, about 0.005%, about 0.01%, about 0.05%, about 0.1%, about 0.5%, about 1%, about 1.1%, about 1.5%, about 1.8%, about 2%, about 3%, about 4%, or about 5%, by weight of the composition or formulation.

In some aspects, the compounds of the present invention are preferably administered topically and delivered in a medically acceptable, substantially sterile, non-irritating ophthalmic preparation. The ophthalmic preparations can contain pharmaceutically acceptable concentrations of salts, buffering agents, preservatives, viscosity modifiers, osmotic agent and delivery enhancing agents. Exemplary non-limiting alts which can be used include sodium chloride, zinc sulfate, and potassium chloride. Exemplary non-limiting buffers which can be used include boric acid and citric acid. Exemplary non-limiting preservatives which can be used include benzalkonium chloride and edetate disodium. Exemplary non-limiting viscosity modifiers which can be used include methyl cellulose, glycerol, and polyethylene glycol. Exemplary non-limiting osmotic agents which can be used include mannitol and sorbitol. Exemplary non-limiting delivery enhancing agents that facilitate the delivery of the therapeutic compound of the invention into the aqueous humor, include substances which increase corneal permeability, such as surfactants, wetting agents, liposomes, DMSO, and the like.

A wetting agent is a substance which facilitates corneal penetration by mildly disrupting the outer corneal surface. In some aspects, the wetting agent is benzalkonium chloride. Other non-limiting examples of wetting agents include sorbitan esters, and polyoxyethylene ethers. It should be understood that although specific formulations have been defined, many variations are possible. The ophthalmic formulations useful in the eye are nonirritating and non-damaging to the eye in the preferred form, and are effective to provide the results desired.

In some aspects, formulations can be applied in a liquid carrier. In some aspects, the carrier is an aqueous carrier. In some aspects, quick dissolving forms of the medicaments may be administered in powder form or rubbed into the eye from applicators of various types. Spraying of the eye, eye drops, and other methods of application can be used.

In some aspects, the preparations are packaged as sterile solutions in dropper bottles, as are standard in ophthalmic formulations. Other containers, including eye cups, can also be used. The preparation can, in some aspects, be packaged with instructions for using the preparation in treating myopia, in some aspects, directing the use of preparation to administer 1 to 2 drops of the solution to each eye.

In some aspects, the compositions can be administered in a pharmaceutically acceptable ophthalmic formulation, such as topically by application of the formulation to the eye in a non-irritating sterile solution or suspension. In that regard, the formulation is preferably at a pH compatible with the eye. In some aspects, a muscarinic antagonist may be selected to act on M receptors of the ciliary muscle with minimal adverse effect mitigated by a miotic agent.

Dosage levels will vary greatly depending upon the individual to be treated, the progression of the disorder, and the specific medicament(s) used. One of ordinary skill in the art, such as a health care provider, can determine proper dosing without undue experimentation and according to standard procedures in the art. Exemplary dosage amounts useful in some embodiments of the methods described herein include 1-2 drops per application. In some embodiments, drop sizes range from about 30 µL to about 80 µL. In some embodiments, exemplary dosage amounts can range from about 30 µL to about 480 µL per application. Exemplary dosage regimens useful in some aspects of the methods described herein include 1 application per day, two applications per day, three applications per day, four applications per day, five applications per day, one application every other day, on application per week, two applications per week, or three applications per week.

In some embodiments, compositions described herein (e.g., compositions having a concentration of from about 0.001% to about 2% (w/v) of a muscarinic receptor antagonist, and/or having a concentration of from about 0.001% to about 5% (w/v) of the miotic agent) can be administer in an application having an amount of from about 1 μL to about 480 μL per application. In some embodiments, application amounts can range from about 10 μL to about 400 μL, from about 20 μL to about 300 μL, from about 20 μL to about 250 μL, from about 20 μL to about 200 μL, from about 20 μL to about 150 μL, from about 20 μL to about 100 μL, from about 25 μL to about 90 μL, from about 25 μL to about 85 μL, from about 30 μL to about 80 μL, from about 25 μL to about 50 μL, from about 25 μL to about 45 μL, from about 25 μL to about 40 μL, from about 30 μL to about 40 μL, from about 55 μL to about 90 μL, from about 60 μL to about 85 μL, or from about 60 μL to about 80 μL per application.

In some embodiments, compositions described herein (e.g., compositions including the muscarinic receptor antagonist, the miotic agent, or a combination thereof) can be administered during a treatment period. In some aspects, exemplary treatment periods include 1 day, up to about 5 days, up to about 10 days, up to about 30 days, up to about 1 week, up to about 2 weeks, up to about 3 weeks, up to about 4 weeks, up to about 5 weeks, up to about 1 month, up to about 2 months, up to about 3 months, up to about 4 months, up to about 5 months, up to about 6 months, up to about 7 months, up to about 8 months, up to about 9 months, up to about 10 months, up to about 11 months, up to about 1 year, up to about 2 years, up to about 3 years, up to about 4 years, up to about 5 years, or up to about 10 years, from about 1 day to about 10 years, from about 1 month to about 10 years, from about 2 months to about 10 years, from about 3 months to about 10 years, from about 4 months to about 10 years, from about 5 months to about 10 years, from about 6 months to about 10 years, from about 6 months to about 9 years, from about 6 months to about 8 years, from about 6 months to about 7 years, from about 6 months to about 6 years, from about 6 months to about 5 years, from about 1 day to about 60 months, from about 6 months to about 4 years, from about 6 months to about 3 years, from about 6 months to about 2 years, from about 6 months to about 1 year, and the like. In some aspects of the methods described herein, treatment regimens may be periodically stopped and restarted according to the subject's needs.

In some aspects, compositions described herein (e.g., compositions including the muscarinic receptor antagonist, the miotic agent, or a combination thereof) can be administered from 1 to 6 times per day, from 1 to 5 times per day, from 1 to 4 times per day, from 1 to 3 times per day, or from 1 to 2 times per day during the treatment period. In some embodiments, compositions described herein (e.g., compositions including the muscarinic receptor antagonist, the miotic agent, or a combination thereof) can be administered to a subject within, e.g., 2 hours, 1 hour, 45 minutes, 30 minutes, 15 minutes, 10 minutes, or 5 minutes prior to a period of sleep for the subject.

Provided herein are methods for inhibiting and/or slowing axial lengthening of an eye of a subject, while minimizing side effects such as, e.g., pupil dilation and/or light sensitivity in the subject. In some aspects, the methods can be useful in treating, e.g., myopia in an effected eye. In some aspects, the compositions and methods can be useful preventing, inhibiting, slowing, or regressing the progression of myopia in an eye while minimizing side effects such as, e.g., pupil dilation and/or light sensitivity in the subject. Exemplary methods include administering to a subject in need of treatment therapeutically effective amounts of any of the compositions described herein comprising a muscarinic receptor antagonist and a miotic agent. Other exemplary methods include administering to the subject, therapeutically effective amounts of each of a muscarinic receptor antagonist and a miotic agent. In some aspects of the methods described herein, the muscarinic receptor antagonist and the miotic agent can be administered concurrently. In some aspects of the methods described herein, the muscarinic receptor antagonist and the miotic agent can be administered subsequently. In some aspects of the methods described herein, the muscarinic receptor antagonist can be administered prior to administering the miotic agent. In some aspects of the methods described herein, the muscarinic receptor antagonist can be administered after the miotic agent. In various aspects of the methods described herein, the methods can treat the disease in the subject.

In some aspects of any of the methods described herein, the subject has or is at risk for developing myopia in at least one eye. For example, in some aspects, methods described herein can also be useful for treatment of myopia. As another example, in some aspects, methods described herein can also be useful for prophylactic treatment of myopia. As used herein, treating includes "prophylactic treatment", which means reducing the incidence of or preventing (or reducing the risk of) a sign or symptom of a disease (e.g., myopia) in a subject at risk of developing a disease (e.g., myopia). The method described herein is suited particularly for subjects who are otherwise free of indications for ophthalmic treatments utilizing a muscarinic agonist or a miotic agent. In some aspects of the methods described herein, the muscarinic receptor antagonist is administered in an amount sufficient to inhibit, slow, or prevent progression of myopia in the eye. In some aspects of the methods described herein, the muscarinic receptor antagonist is administered in an amount sufficient to inhibit or slow growth in the axial length of the eye. In some aspects of the methods described herein, the miotic agent is administered in an amount sufficient to maintain pupillary dilation of e.g., less than about 8 mm, less than about 7.9 mm, less than about 7.8 mm, less than about 7.7 mm, less than about 7.6 mm, less than about 7.5 mm, less than about 7.4 mm, less than about 7.3 mm, less than about 7.25 mm, less than about 7.2 mm, less than about 7.1 mm, less than about 7 mm, less than about 6.8 mm, less than about 6.75 mm, less than about 6.5 mm, less than about 6.4 mm, less than about 6.3 mm, less than about 6.25 mm, less than about 6.2 mm, less than about 6.1 mm, or less than about 6 mm in diameter.

In some aspects, methods described herein can include treating the eye with an ocular device during the treatment period. In some aspects, the ocular device can be a lens, such as a contact lens, an implanted lens, or a lens associated with external devices such as glasses. In some aspects the ocular device can be a corrective lens. In some aspects, a contact lenses or implantable lenses may contain or be treated with any of the compositions described herein to provide a route of administration for the compositions.

In some aspects of the methods described herein parasympathetic/cholinergic/ciliary contraction in the subject's eye are decreased in order to allow normal accommodation for myopic eye. Without wishing to be bound by theory, it is believed this action of the ciliary muscle under parasympathetic innervation provides for zonules constriction, which can allow the lens to assume a less spherical shape.

In some aspects, a method can include administering to a myopic subject an effective amount of a muscarinic antagonist in combination with a miotic agent. The selection of muscarinic antagonist in combination with a miotic agent can slow down the progression of myopia and minimize the effects on pupillary muscle to reduce the potential adverse effects.

Compositions described herein can include additional therapeutic agents. Methods described herein can also include administration of additional therapeutic agents. The term "therapeutic agent" refers to a therapeutic treatment that involves administering to a subject a therapeutic agent that is known to be useful in the treatment of a disease, e.g., myopia, or known to be useful in providing a therapeutic benefit to one or more ocular diseases, discomforts, or symptoms, whether associated with a particular ocular disease or not. In some aspects, a therapeutic agent can increase comfort of a subject eyes. For example, a therapeutic agent can include a substance known to alleviate dry eyes in a subject.

Non-limiting examples of therapeutic agents include antibiotics, steroids, artificial tears, intra-ocular pressure (IOP) lowering agents, immunosuppressants, dry eye-treating agents, and the like.

Also provided herein are kits that include a composition or formulation having a muscarinic receptor antagonist, and a composition or formulation having a miotic agent. In some instances, the kits can include instructions for performing any of the methods described herein. In some aspects, the kits can include at least one dose of any of the pharmaceutical compositions described herein. The kits described herein are not so limited; other variations will be apparent to one of ordinary skill in the art.

EMBODIMENTS

Embodiment 1. A composition comprising:
a muscarinic receptor antagonist; and
a miotic agent.

Embodiment 2. The composition of embodiment 1, wherein the muscarinic receptor antagonist is selected from the group consisting of a non-selective muscarinic receptor antagonist and a selective M3 muscarinic receptor antagonist.

Embodiment 3. The composition of any one of embodiments 1 or 2, wherein the muscarinic receptor antagonist is a non-selective muscarinic receptor antagonist selected from the group consisting of atropine, cyclopentolate, homatropine, hyoscine, pirenzapine, anisodamine, tropicamide, pharmaceutically acceptable salts thereof, and combinations thereof.

Embodiment 4. The composition of any one of embodiments 1 or 2, wherein the muscarinic receptor antagonist is a selective M3 muscarinic receptor antagonist selected from the group consisting of darifenacin, tiotropium, zamifenacin, J104129, DAU5884, pharmaceutically acceptable salts thereof, and combinations thereof.

Embodiment 5. The composition of any one of embodiments 1-4, wherein the miotic agent is selected from the group consisting of an alpha-1 adrenergic receptor antagonist, an alpha-2 adrenergic receptor agonist, a beta-adrenergic receptor antagonist, a nicotine receptor agonist, an antipsychotic, an anti-emetic, a cannabinoid, an MAO inhibitor, an EP1 receptor agonist, an EP4 receptor agonist, an FP receptor agonist, a calcium channel modulator, and combinations thereof.

Embodiment 6. The composition of any one of embodiments 1-5, wherein the miotic agent is an alpha-1 adrenergic receptor antagonist.

Embodiment 7. The composition of any one of embodiments 1-5, wherein the miotic agent is selected from the group consisting of dapiprazole, thymoxamine, brimonidine, nicotine, apraclonidin, phentolamine, pharmaceutically acceptable salts thereof, and combinations thereof.

Embodiment 8. The composition of any one of embodiments 1-7, wherein the muscarinic receptor antagonist is present in a concentration of from about 0.001% to about 2% (w/v).

Embodiment 9. The composition of any one of embodiments 1-8, wherein the miotic agent is present in a concentration of from about 0.001% to about 5% (w/v).

Embodiment 10. The composition of any one of embodiments 1-9, further comprising a viscosity enhancer.

Embodiment 11. The composition of embodiment 10, wherein the viscosity enhancer is selected from the group consisting of carboxymethyl cellulose, hydroxypropylmethyl cellulose, or a combination thereof.

Embodiment 12. The composition of any one of embodiments 1-11, further comprising a surfactant.

Embodiment 13. The composition of embodiment 12, wherein the surfactant is selected from the group consisting of an anionic surfactant, a nonionic surfactant, and a combination thereof.

Embodiment 14. The composition of embodiment 13, wherein the anionic surfactant is selected from the group consisting of a gamma cyclodextrin, sulfobutylether β-cyclodextrin, sodium lauryl sulfate, sodium ester lauryl sulfate, and combinations thereof.

Embodiment 15. The composition of embodiment 13, wherein the nonionic surfactant is selected from the group consisting of a poloxamer, a polysorbate, sorbitan monolaurate, sorbitan monopalmitate, sorbitan monostearate, sorbitan monooleate, polyoxyl stearate, a polyoxyl alkyl, a cyclodextrin, a derivative of a cyclodextrin, and combinations thereof.

Embodiment 16. The composition of embodiment 12, wherein the surfactant is selected from the group consisting of sulfobutylether β-cyclodextrin, polyoxyl 40 stearate, 2-hydroxypropyl beta-cyclodextrin, and combinations thereof.

Embodiment 17. The composition of any one of embodiments 1-16, wherein:
the muscarinic receptor agonist is atropine or a pharmaceutically acceptable salt thereof; and
the miotic agent is brimonidine or a pharmaceutically acceptable salt thereof.

Embodiment 18. The composition of any one of embodiments 1-16, wherein:
the muscarinic receptor agonist is atropine or a pharmaceutically acceptable salt thereof; and
the miotic agent is bunazosin or a pharmaceutically acceptable salt thereof.

Embodiment 19. The composition of any one of embodiments 1-16, wherein:
the muscarinic receptor agonist is atropine or a pharmaceutically acceptable salt thereof; and
the miotic agent is thymoxamine or a pharmaceutically acceptable salt thereof.

Embodiment 20. The composition of any one of embodiments 1-16, wherein:
the muscarinic receptor agonist is atropine or a pharmaceutically acceptable salt thereof; and
the miotic agent is apraclonidine or a pharmaceutically acceptable salt thereof.

Embodiment 21. The composition of any one of embodiments 1-16, wherein:
the muscarinic receptor agonist is atropine or a pharmaceutically acceptable salt thereof; and
the miotic agent is phentolamine or a pharmaceutically acceptable salt thereof.

Embodiment 22. The composition of any one of embodiments 1-21, wherein the composition is an ophthalmological composition.

Embodiment 23. A method comprising administering to an eye of a subject, during a treatment period:
a muscarinic receptor antagonist; and
a miotic agent.

Embodiment 24. The method of embodiment 23, wherein the eye of the subject is myopic or is at risk for developing myopia.

Embodiment 25. The method of any one of embodiments 23 or 24, wherein the muscarinic receptor antagonist is administered in an amount sufficient to inhibit, slow, or prevent progression of myopia in the eye, modulate the accommodation of the eye, or combinations thereof.

Embodiment 26. The method of any one of embodiments 23-25, wherein the muscarinic receptor antagonist is administered in an amount sufficient to inhibit or slow growth in the axial length of the eye, modulate the accommodation of the eye, or combinations thereof.

Embodiment 27. The method of any one of embodiments 23-26, wherein the miotic agent is administered in an amount sufficient to maintain pupillary dilation of less than about 7.5 mm in diameter.

Embodiment 28. The method of any one of embodiments 23-27, wherein the muscarinic receptor antagonist and the miotic agent are administered concurrently.

Embodiment 29. The method of any one of embodiments 23-27, wherein the muscarinic receptor antagonist and the miotic agent are administered sequentially.

Embodiment 30. The method of any one of embodiments 23-29 wherein the muscarinic receptor antagonist is selected from the group consisting of a non-selective muscarinic receptor antagonist and a selective M3 muscarinic receptor antagonist.

Embodiment 31. The method of any one of embodiments 23-30, wherein the muscarinic receptor antagonist is a non-selective muscarinic receptor antagonist selected from the group consisting of atropine, cyclopentolate, homatropine, hyoscine, pirenzapine, anisodamine, tropicamide, pharmaceutically acceptable salts thereof, and combinations thereof.

Embodiment 32. The method of any one of embodiments 23-30, wherein the muscarinic receptor antagonist is a selective M3 muscarinic receptor antagonist selected from the group consisting of darifenacin, tiotropium, zamifenacin, J104129, DAU5884, pharmaceutically acceptable salts thereof, and combinations thereof.

Embodiment 33. The method of any one of embodiments 23-32, wherein the miotic agent is selected from the group consisting of an alpha-1 adrenergic receptor antagonist, an alpha-2 adrenergic receptor agonist, a beta-adrenergic receptor antagonist, a nicotine receptor agonist, an antipsychotic, an anti-emetic, a cannabinoid, an MAO inhibitor, an EP1 receptor agonist, an EP4 receptor agonist, an FP receptor agonist, a calcium channel modulator, and combinations thereof.

Embodiment 34. The method of any one of embodiments 23-33, wherein the miotic agent is selected from the group consisting of dapiprazole, thymoxamine, brimonidine, nicotine, apraclonidin, phentolamine, pharmaceutically acceptable salts thereof, and combinations thereof.

Embodiment 35. The method of any one of embodiments 23-34, wherein the muscarinic receptor antagonist is administered in a composition having a concentration of from about 0.001% to about 2% (w/v) of the muscarinic receptor antagonist.

Embodiment 36. The method of any one of embodiments 23-35, wherein the miotic agent is administered in a composition having a concentration of from about 0.001% to about 5% (w/v) of the miotic agent.

Embodiment 37. The method of embodiment 23-36, wherein the muscarinic receptor antagonist is administered in an application in an amount of about 30 μL to about 80 μL per application of a composition having a concentration of from about 0.001% to about 2% (w/v) of the muscarinic receptor antagonist.

Embodiment 38. The method of embodiments 23-37, wherein the miotic agent is administered in an application in an amount of about 30 μL to about 80 μL per application of a composition having a concentration of from about 0.001% to about 5% (w/v) of the miotic agent.

Embodiment 39. The method of any one of embodiments 23-38, wherein the treatment period is from about 1 day to about 60 months.

Embodiment 40. The method of any one of embodiments 23-39, wherein the muscarinic receptor antagonist, the miotic agent, or a combination thereof is administered from 1 to 6 times per day during the treatment period.

Embodiment 41. The method of any one of embodiments 23-40, further comprising treating the eye with an ocular device during at least a portion of the treatment period.

Embodiment 42. The method of embodiment 41, wherein the ocular device is a lens.

Embodiment 43. The method of embodiment 41, wherein the ocular device is a corrective lens.

Embodiment 44. The method of any one of embodiments 23-43, further comprising correcting vision in the eye with a corrective lens during the treatment period.

Embodiment 45. A method comprising administering to an eye of a subject, during a treatment period, a therapeutically effective amount of the composition of any one of claims 1-22.

Embodiment 46. The method of embodiment 45, wherein the eye of the subject is myopic or is at risk for developing myopia.

Embodiment 47. The method of any one of embodiments 45 or 46, wherein the muscarinic receptor antagonist is administered in an amount sufficient to inhibit, slow, or prevent progression of myopia in the eye.

Embodiment 48. The method of any one of embodiments 45-47, wherein the muscarinic receptor antagonist is administered in an amount sufficient to inhibit or slow growth in the axial length of the eye.

Embodiment 49. The method of any one of embodiments 45-48, wherein the miotic agent is administered in an amount sufficient to maintain pupillary dilation of less than about less than about 7.5 mm in diameter.

Embodiment 50. The method of embodiments 45-49, wherein the composition is administered in an application in an amount of about 30 μL to about 80 μL per application.

Embodiment 51. The method of any one of embodiments 45-50, wherein the treatment period is from about 1 day to about 60 months.

Embodiment 52. The method of any one of embodiments 45-51, wherein composition is administered from 1 to 6 times per day during the treatment period.

Embodiment 53. The method of any one of embodiments 45-52, further comprising treating the eye with an ocular device during at least a portion of the treatment period.

Embodiment 54. The method of embodiment 53, wherein the ocular device is a lens or an implant.

Embodiment 55. The method of embodiment 53, wherein the ocular device is a corrective lens.

Embodiment 56. The method of any one of embodiments 45-55, further comprising correcting vision in the eye with a corrective lens during the treatment period.

EXAMPLES

The invention is further described in the following examples, which do not limit the scope of the invention described in the claims.

Example 1

Various formulations are tested for efficacy.

Formulations

A base solution can be formulated as follows: Sodium Chloride 0.3%; Edetate Disodium 0.1%; Boric Acid 1.0%; Benzalkonium Chloride 0.01% Sodium Hydroxide (adjust to pH 7.0) and Water. Muscarinic receptor antagonist and miotic agent, at a certain concentration, is added to the base solution.

Method

The formulations shown in Table 1 are administered to the eye of a human adolescent or adult with myopia, shown by his/her discomfort when reading, or inability to read fine print in distance. Vision is improved after administration of the eye drops. One drop of the ophthalmic solution is administered topically to the eye of a myopic, before and after Hartinger Refractometry at distance is performed by the same observer. The pupil size is measured by pupillometer. Refraction at distance is performed with the Hartinger Refractomer by the same observer prior to instillation of ophthalmic solutions. The pupil size is measured by pupillometer. At baseline prior to installation of ophthalmic solutions, refraction and pupil size are measured in the right eye and in the left eye at distance. At 30, 60, and 120 minute post installation ophthalmic solutions, refraction and pupil size are measured in the right eye and in the left eye at distance. In the myopic eye, the change in the distance and near myopic correction will be evaluated. The pupil size is also evaluated. The selected ophthalmic solution is also evaluated for longer term treatment.

The compositions 1-5 in Table 4 are tested for the efficacy of the muscarinic receptor antagonists:

TABLE 4

| | Formulation # | | | | |
|---|---|---|---|---|---|
| | 1 | 2 | 3 | 4 | 5 |
| Atropin Sulfate | 0.01% | 0.10% | | | |
| Hyocine | | | 0.01% | | |
| Cyclopentolate | | | | 0.50% | |
| Darifenacin | | | | | 0.50% |
| Sodium Chloride | 0.30% | 0.30% | 0.30% | 0.30% | 0.30% |
| Edetate Disodium | 0.10% | 0.10% | 0.10% | 0.10% | 0.10% |
| Boric Acid | 1.00% | 1.00% | 1.00% | 1.00% | 1.00% |
| Benzalkonium Chloride | 0.01% | 0.01% | 0.01% | 0.01% | 0.01% |
| Sodium Hydroxide | adj pH = 7.0 | adj pH = 7.0 | adj pH = 7.0 | adj pH = 7.0 | adj pH = 7.0 |
| Water | qs | qs | qs | qs | qs |

Example 2

The short-term effects of atropine and miotic agents on pupil size, accommodation and visual acuity were investigated in healthy volunteers.

Formulation

Five ophthalmic formulations were prepared as described in Table 5 below. All formulations turned out to be clear aqueous solution.

TABLE 5

| | Formulation | | | | |
|---|---|---|---|---|---|
| | 1 | 2 | 3 | 4 | 5 |
| Atropin Sulfate | 0.10% | 0.10% | 0.10% | 0.10% | 0.10% |
| Brimonidine tartrate | 0.20% | | | | |
| Bunazosin HCl | | 0.30% | | | |
| Thymoxamine HCl | | | 0.50% | | |
| Apraclonidine HCl | | | | 0.50% | |
| Phentolamine mesylate | | | | | 0.80% |
| Sodium Chloride | 0.30% | 0.30% | 0.30% | 0.30% | 0.30% |
| EDTA Edetate Disodium | 0.10% | 0.10% | 0.10% | 0.10% | 0.10% |
| Boric Acid | 1.00% | 1.00% | 1.00% | 1.00% | 1.00% |
| Benzalkonium Chloride | 0.01% | 0.01% | 0.01% | 0.01% | 0.01% |
| Sodium Hydroxide | adj pH = 7.0 | adj pH = 7.0 | adj pH = 7.0 | adj pH = 7.0 | adj pH = 7.0 |
| Water | qs | qs | qs | qs | qs |

Procedure

Subjects aged 18 to 45 years with myopic refraction of less than −3.5 D in both eyes, healthy without other diseases, without history of allergy, were enrolled and signed study consent. Subjects with ocular disease, cardiovascular disease, or family history of cardiovascular disease, were excluded from this study.

Each cohort included 5 subjects. The same subjects received each of the formulations. There was at least one-week washout period between each treatment. The study was open-label.

Before the drug administration, pupil size, vision acuity at short and long distance, and accommodation were measured. Each subject was administered one drop of the above formulations to each eye. Then the same parameters were measured at 2, 7, and 24 hours post dose. Pupil size was measured by cornea topography. Accommodation was measured by push-out method. Best corrected visual acuity, logMAR, was measured at 0.4 and 5.0 meter under normal daylight.

Results

Results are shown in Table 6 below.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting, slowing, or preventing progression of myopia in the eye, the method comprising administering to an eye of a subject, during a treatment period, a composition comprising:
a non-selective muscarinic receptor antagonist comprising one or more of cyclopentolate, homatropine, hyoscine, amidoamine, or a pharmaceutically acceptable salt thereof; and
a miotic agent comprising one or more of brimonidine, bunazosin, thymoxamine, apraclonidine, and phentolamine, or a pharmaceutically acceptable salt thereof.

TABLE 6

| | Pre-dose | | | | 2 hours | | | | 7 hours | | | | 24 hours | | | |
|---|---|---|---|---|---|---|---|---|---|---|---|---|---|---|---|---|
| | Accommodation (cm) | | Pupil Size (mm) | | Accommodation (cm) | | Pupil Size (mm) | | Accommodation (cm) | | Pupil Size (mm) | | Accommodation (cm) | | Pupil Size (mm) | |
| Subject # | OD | OS | OD | OS | OD | OS | OD | OS | OD | OS | OD | OS | OD | OS | OD | OS |
| Atropin Sulfate(0.1%), Brimonidine tartrate (0.2%) | | | | | | | | | | | | | | | | |
| 1 | 11 | 12 | 4.8 | 4.9 | 39 | 43 | 6.9 | 6.9 | >52 | >52 | 7.0 | 6.9 | >52 | >52 | 6.2 | 6.5 |
| 2 | 11 | 10 | 5.1 | 5.9 | 18 | 18 | 7.1 | 7.2 | 25 | 23 | 7.0 | 7.0 | 23 | 23 | 6.2 | 6.4 |
| 3 | 9 | 8 | 5.1 | 5.4 | 13 | 16 | 6.3 | 6.8 | 12 | 42 | 7.0 | 7.2 | 12 | 32 | 6.3 | 7.0 |
| 4 | 13 | 13 | 4.4 | 4.2 | 24 | 26 | 7.1 | 7.0 | 52 | 52 | 6.9 | 6.8 | 36 | 40 | 5.9 | 6.1 |
| 5 | 9 | 10 | 4.4 | 5.7 | 17 | 15 | 7.2 | 7.2 | 20 | 19 | 7.4 | 7.2 | 15 | 15 | 6.3 | 6.6 |
| Average | 10.6 | 10.6 | 4.76 | 5.22 | 22.2 | 23.6 | 6.92 | 7.02 | 27.25 | 34 | 7.06 | 7.02 | 21.5 | 27.5 | 6.18 | 6.52 |
| Atropin Sulfate(0.1%), Bunazosin HCl (0.3%) | | | | | | | | | | | | | | | | |
| 1 | 10 | 10 | 5.3 | 5.1 | 12 | 12 | 7.9 | 7.9 | 12 | 12 | 7.8 | 8.2 | 11 | 12 | 6.5 | 6.9 |
| 2 | 10 | 9 | 5.5 | 6.2 | 14 | 12 | 7.8 | 7.9 | 13 | 13 | 7.6 | 7.9 | 13 | 11 | 7.4 | 7.2 |
| 3 | 9 | 8 | 6.0 | 6.0 | 11 | 11 | 7.0 | 7.9 | 11 | 11 | 6.9 | 7.6 | 9 | 13 | 5.9 | 7.3 |
| 4 | 10 | 10 | 4.3 | 4.0 | 15 | 14 | 7.8 | 7.6 | 19 | 19 | 7.5 | 7.7 | 15 | 16 | 6.2 | 5.5 |
| 5 | 8 | 9 | 5.0 | 5.2 | 11 | 10 | 8.1 | 7.7 | 12 | 12 | 7.7 | 7.8 | 11 | 12 | 7.1 | 7.1 |
| Average | 9.4 | 9.2 | 5.2 | 5.3 | 12.6 | 11.8 | 7.7 | 7.8 | 13.4 | 13.4 | 7.5 | 7.8 | 11.8 | 12.8 | 6.6 | 6.8 |
| Atropin Sulfate(0.1%), Thymoxamine HCl (0.5%) | | | | | | | | | | | | | | | | |
| 1 | 12 | 12 | 5.0 | 5.2 | 13.0 | 13.0 | 6.3 | 7.3 | 13.0 | 14.0 | 6.0 | 6.4 | 13.0 | 13.0 | 4.3 | 5.0 |
| 2 | 11 | 11 | 5.2 | 5.2 | 14.0 | 13.0 | 5.9 | 6.8 | 14.0 | 14.0 | 6.1 | 6.6 | 11.0 | 12.0 | 4.6 | 5.2 |
| 3 | 12 | 12 | 4.6 | 4.7 | 13.0 | 13.0 | 5.5 | 6.0 | 12.0 | 13.0 | 5.7 | 5.9 | 12.0 | 12.0 | 5.4 | 5.3 |
| 4 | 14 | 14 | 3.8 | 3.7 | 14.0 | 14.0 | 6.9 | 6.6 | 13.0 | 12.0 | 6.2 | 6.3 | 13.0 | 13.0 | 4.1 | 4.2 |
| 5 | 10 | 10 | 4.6 | 5.4 | 12.0 | 12.0 | 7.0 | 7.1 | 12.0 | 12.0 | 6.8 | 6.5 | 11.0 | 11.0 | 4.8 | 5.1 |
| Average | 11.8 | 11.8 | 4.6 | 4.8 | 13.2 | 13.0 | 6.3 | 6.8 | 12.8 | 13.0 | 6.2 | 6.3 | 12.0 | 12.2 | 4.6 | 5.0 |
| Atropin Sulfate(0.1%), Apraclonidine HCl (0.5%) | | | | | | | | | | | | | | | | |
| 1 | 12 | 13 | 5.2 | 5.4 | 19 | 20 | 7.8 | 7.7 | 40 | 30 | 7.9 | 7.7 | 25 | 18 | 7.6 | 7.1 |
| 2 | 10 | 9 | 5.8 | 6.8 | 19 | 21 | 7.6 | 7.7 | 18 | 28 | 7.6 | 7.7 | 26 | 37 | 6.8 | 7.1 |
| 3 | 9 | 9 | 5.1 | 5.5 | 14 | 16 | 6.6 | 6.9 | 21 | 28 | 7.1 | 7.1 | 17 | 34 | 6.8 | 7.3 |
| 4 | 12 | 12 | 3.8 | 3.8 | 38 | 35 | 7.8 | 8.0 | >52 | >52 | 8.8 | 8.5 | >52 | >52 | 7.4 | 7.5 |
| 5 | 9 | 9 | 4.8 | 5.0 | 24 | 21 | 8.5 | 8.0 | 33 | 31 | 8.4 | 7.8 | 28 | 26 | 7.3 | 7.3 |
| Average | 10.4 | 10.4 | 4.9 | 5.3 | 22.8 | 22.6 | 7.7 | 7.7 | 28.0 | 29.3 | 8.0 | 7.8 | 24.0 | 28.8 | 7.2 | 7.3 |
| Atropin Sulfate(0.1%), Phentolamine (0.8%) | | | | | | | | | | | | | | | | |
| 1 | 11 | 12 | 5.4 | 5.1 | 12 | 12 | 7.5 | 7.4 | 13 | 12 | 7.1 | 6.8 | 12 | 12 | 6.3 | 6.0 |
| 2 | 11 | 9 | 5.9 | 6.0 | 12 | 11 | 7.5 | 7.5 | 14 | 12 | 7.3 | 7.2 | 13 | 14 | 6.6 | 6.4 |
| 3 | 9 | 9 | 5.9 | 5.9 | 10 | 11 | 6.4 | 6.3 | 11 | 12 | 6.0 | 6.1 | 12 | 13 | 5.6 | 5.7 |
| 4 | 13 | 12 | 4.8 | 4.7 | 14 | 14 | 7.5 | 7.4 | 17 | 17 | 7.1 | 7.1 | 16 | 17 | 5.4 | 5.1 |
| 5 | 9 | 9 | 5.0 | 5.4 | 11 | 11 | 7.3 | 7.3 | 12 | 12 | 7.2 | 7.0 | 11 | 11 | 6.1 | 6.2 |
| Average | 10.6 | 10.2 | 5.4 | 5.42 | 11.8 | 11.8 | 7.24 | 7.18 | 13.4 | 13 | 6.94 | 6.84 | 12.8 | 13.4 | 6 | 5.88 |

2. The method of claim 1, wherein the non-selective muscarinic receptor antagonist is present in a concentration of about 0.001% to about 2% (w/v).

3. The method of claim 2, wherein the non-selective muscarinic receptor antagonist is present in a concentration of about 0.001% to about 1.5% (w/v).

4. The method of claim 1, wherein:
the muscarinic receptor antagonist is administered in an amount sufficient to inhibit or slow growth in the axial length of the eye,
the muscarinic receptor antagonist is administered in an amount sufficient to modulate the accommodation of the eye, and
the miotic agent is administered in an amount sufficient to maintain pupillary dilation of less than about 7.5 mm in diameter, and any combination thereof.

5. The method of claim 1, wherein the non-selective muscarinic receptor antagonist is cyclopentolate.

6. The method of claim 1, wherein the non-selective muscarinic receptor antagonist is homatropine.

7. The method of claim 1, wherein the non-selective muscarinic receptor antagonist is hyoscine.

8. The method of claim 1, wherein the non-selective muscarinic receptor antagonist is anisodamine.

9. The method of claim 1, wherein the non-selective muscarinic receptor antagonist and the miotic agent are administered concurrently.

10. The method of claim 1, wherein the non-selective muscarinic receptor antagonist and the miotic agent are administered sequentially.

11. The method of claim 1, wherein the non-selective muscarinic receptor antagonist, the miotic agent, or a combination thereof is administered from 1 to 6 times per day during the treatment period; or wherein the treatment period is from about 1 day to about 60 months.

12. The method of claim 1, further comprising a viscosity enhancer, a surfactant, or a combination thereof.

13. The method of claim 1, further comprising treating the eye with an ocular device during at least a portion of the treatment period.

14. The method of claim 13, wherein the ocular device is a lens or an implant.

15. The method of claim 1, further comprising correcting vision in the eye with a corrective lens during the treatment period.

* * * * *